(12) United States Patent
Kim

(10) Patent No.: US 8,517,946 B2
(45) Date of Patent: Aug. 27, 2013

(54) USER INTERFACE IN AN ULTRASOUND SYSTEM

(75) Inventor: Hyoung Jin Kim, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 209 days.

(21) Appl. No.: 12/413,024

(22) Filed: Mar. 27, 2009

(65) Prior Publication Data

US 2009/0247874 A1    Oct. 1, 2009

(30) Foreign Application Priority Data

Mar. 28, 2008   (KR) ........................ 10-2008-0028801

(51) Int. Cl.
*A61B 8/00* (2006.01)

(52) U.S. Cl.
USPC ........... 600/443; 600/407; 600/437; 345/649; 348/333.12

(58) Field of Classification Search
USPC ......... 600/407, 437, 440, 442, 446; 345/649, 345/657, 669; 348/333.01, 333.05–333.06, 348/333.11–333.12
See application file for complete search history.

(56) References Cited

U.S. PATENT DOCUMENTS

| | | | |
|---|---|---|---|
| 6,063,030 A | | 5/2000 | Vara et al. |
| 6,516,215 B1 | | 2/2003 | Roundhill |
| 6,891,920 B1 * | | 5/2005 | Minyard et al. ................ 378/37 |
| 7,129,963 B2 * | | 10/2006 | Bohnisch et al. ............. 345/649 |
| 2005/0041147 A1 * | | 2/2005 | Kim et al. ..................... 348/511 |
| 2006/0116578 A1 * | | 6/2006 | Grunwald et al. ............ 600/440 |
| 2007/0159549 A1 * | | 7/2007 | Matsumoto ............. 348/333.11 |
| 2007/0176895 A1 * | | 8/2007 | Miyasaka et al. ............ 345/156 |
| 2007/0271528 A1 * | | 11/2007 | Park et al. ..................... 715/810 |

FOREIGN PATENT DOCUMENTS

| | | |
|---|---|---|
| JP | H-10-71146 | 3/1998 |
| JP | 2005-323925 | 11/2005 |
| JP | 2006-26256 | 2/2006 |
| JP | 2006-347478 | 12/2006 |
| JP | 2007-020839 | 2/2007 |
| JP | 2008-029468 | 2/2008 |
| JP | 2008-515583 | 5/2008 |
| KR | 10-2006-0106054 | 10/2006 |

OTHER PUBLICATIONS

Office Action issued Dec. 6, 2010 in Korean Application No. 10-2008-0028801.
Office Action dated Jun. 4, 2013 issued in Japanese appln. 2009-076723.

* cited by examiner

*Primary Examiner* — James Kish
*Assistant Examiner* — Michael N Fisher
(74) *Attorney, Agent, or Firm* — Oblon, Spivak, McClelland, Maier & Neustadt, L.L.P.

(57) ABSTRACT

Embodiments of a user interface in an ultrasound system are disclosed. In one embodiment, the ultrasound system comprises a display unit for prompting a user to touch a desired one of hierarchically arranged soft buttons for triggering an execution of the function of the ultrasound system associated with the touched button. The display unit includes a display having a display with touch panel mounted. The display unit is configured to display a touch screen menu together with the ultrasound image on the display.

10 Claims, 8 Drawing Sheets

USER INTERFACE IN AN ULTRASOUND SYSTEM

The present application claims priority from Korean Patent Application No. 10-2008-0028801 filed on Mar. 28, 2008, the entire subject matter of which is incorporated herein by reference.

TECHNICAL FIELD

The present disclosure generally relates to user interfaces, and more particularly to a user interface adapted to utilize a touch screen in an ultrasound system.

BACKGROUND

Recently, an ultrasound system has been extensively used in the medical field due to its non-invasive and non-destructive nature. Modern high-performance ultrasound imaging systems and techniques are commonly used to produce two dimensional ultrasound images, three-dimensional ultrasound images and color flow images of internal features of patients. Further, such ultrasound systems provide various functions such as image recording, image annotation, zooming, archiving, panning and the like.

As the number of functions performed by the ultrasound system is increased, the size of a user interface such as a control panel, on which a keyboard, a track ball and slide bars are installed, is also inevitably increased. However, it is difficult to expand the area of the user interface due to the limited space of the ultrasound system. To resolve this problem, the ultrasound system may provide a touch screen as the user interface. The touch screen may be mounted on a control panel in the conventional ultrasound system. In order to install the touch screen on the ultrasound system, a touch panel liquid crystal display and an additional graphic card should be additionally provided. Thus, installing the touch screen on the control panel significantly increases the manufacturing costs.

Further, the ultrasound system may use a display, the horizontal size of which is relatively lager than the vertical size (e.g., the aspect ratio is 4:3 or 16:9). However, there is a problem since a display area of the display is not efficiently used due to the characteristics of the ultrasound image.

SUMMARY

Embodiments of a user interface, which utilizes a touch screen in an ultrasound system, are disclosed herein. In one embodiment, by way of non-limiting example, an ultrasound system comprises: an ultrasound diagnostic unit for forming an ultrasound image based on echoes reflected from a target object; a touch screen menu forming unit for forming a touch screen menu having graphics and text, the touch screen menu including hierarchically arranged soft buttons associated with functions of the ultrasound system; and a display unit including a display with a touch panel mounted, the display unit being configured to display the touch screen menu together with the ultrasound image on the display to prompt a user to touch a desired one of the soft buttons for triggering an execution of the associated function therewith, wherein a display area of the display is horizontally divided into an upper display area and a lower display area, wherein the ultrasound image is displayed on the upper display area and the touch screen menu is displayed on the lower display area.

In another embodiment, an ultrasound system comprises: an ultrasound diagnostic unit for forming an ultrasound image based on echoes reflected from a target object; a touch screen menu forming unit for forming a touch screen menu having graphics and text, the touch screen menu including hierarchically arranged soft buttons associated with functions of the ultrasound system; and a display unit including a display with a touch panel mounted, the display unit being configured to display the touch screen menu together with the ultrasound image on the display to prompt a user to touch a desired one of the soft buttons for triggering an execution of the associated function therewith, the display unit further including a support to rotatably support the display; a rotation detection unit configured to detect rotation of the display to output a rotation detection signal; and a control unit configured to determine a display mode of the ultrasound image and the touch screen menu in response to the rotation detection signal.

In another embodiment, an ultrasound system comprises: an ultrasound diagnostic unit for forming an ultrasound image based on echoes reflected from a target object; a touch screen menu forming unit for forming a touch screen menu having graphics and text, the touch screen menu including hierarchically arranged soft buttons associated with functions of the ultrasound system; a display unit including a display with a touch panel mounted, the display unit being configured to display the touch screen menu together with the ultrasound image on the display to prompt a user to touch a desired one of the soft buttons for triggering an execution of the associated function therewith, the display unit further including a support to rotatably support the display; a rotation detection unit configured to detect rotation of the display to output a rotation detection signal; an approach sensing unit mounted on the display unit, the approach sensing unit being configured to sense an approach of an object to output an approach sensing signal while the object is within a predetermined distance from the display; and a control unit configured to determine a display mode of the ultrasound image and the touch screen menu in response to the rotation detection signal and the approach sensing signal.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
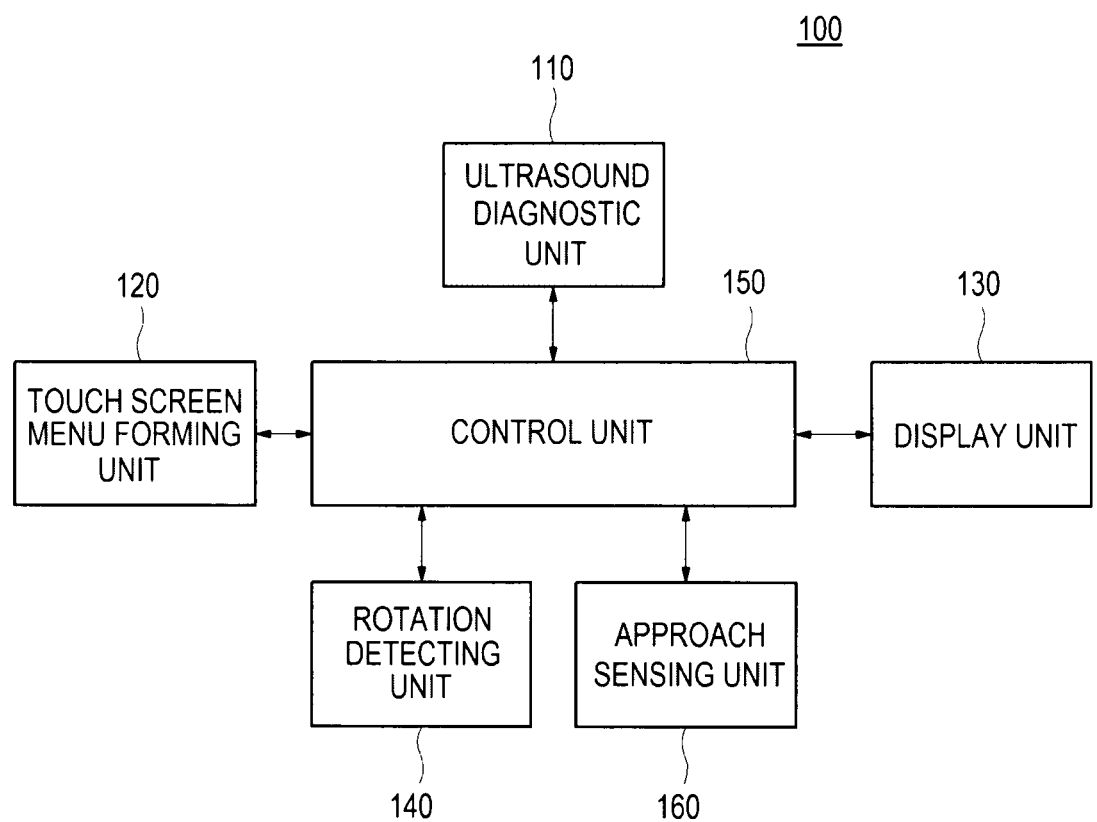
FIG. 1 is a block diagram showing an illustrative embodiment of an ultrasound system.

Referring more particularly to FIG. 1, an illustrative embodiment of an ultrasound system 100 is shown. As depicted, the ultrasound system 100 may include an ultrasound diagnostic unit 110 configured to form ultrasound images based on ultrasound echoes reflected from a target object. The ultrasound diagnostic unit 110 may include a probe (not shown) for transmitting and receiving ultrasound signals, a beam former (not shown) for forming a receive beam based on the ultrasound echoes, and an image processing unit (not shown) for processing the receive beam to form the ultrasound image of the target object.

The ultrasound system 100 may further include a touch screen menu forming unit 120 that may be operable to form a touch screen menu having graphics and text. The touch screen menu may include hierarchically arranged soft buttons associated with functions of the ultrasound system. For example, the touch screen menu may be classified into a main menu and a sub menu. The main menu may include image mode buttons for selecting the ultrasound image modes such as a 2-dimensional (2D) mode, a color mode, a Power Doppler mode and a pulsed wave mode, and a utility mode for setup of the ultrasound system 100. The sub menu may include a plurality of image adjusting buttons and a plurality of setup buttons associated with the respective soft buttons contained in the main menu. The instructions may include requests for display mode selection, patient information display, rotation of an ultrasound image, enlargement and reduction, gain adjustment, measurement, movement of a cursor and the like.

The ultrasound system may further include a display unit 130 that may display an ultrasound image formed in the ultrasound diagnosing unit 110. Also, the display unit 130 may further display the touch screen menu formed in the touch screen menu forming unit 120. In one embodiment, the display unit 130 may include a display with a touch panel mounted, such as a touch panel liquid crystal display (LCD). The touch panel may be configured to detect a user touch to thereby output a touch signal corresponding to a touch location of the user on the display. That is, the display is configured to display the touch screen menu together with the ultrasound image on the display panel to prompt a user to touch a desired one of the hierarchically arranged soft buttons for triggering an execution of the associated function therewith. The display unit 130 may further include a support to rotatably support the display in a predetermined direction within a predetermined angle by the user.

Figure 2:
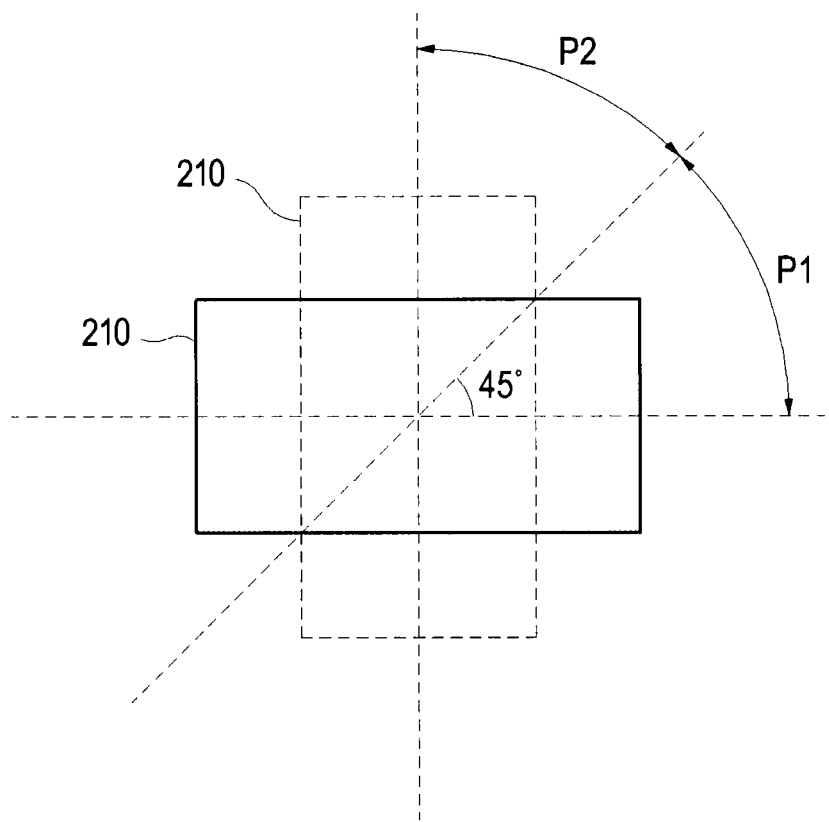
FIG. 2 is a schematic diagram showing an example of rotation of a display.

The ultrasound system 100 may additionally include a rotation detecting unit 140. The rotation detecting unit 140 may be configured to detect a rotation of the display in the display unit 130 to thereby output a detection signal ("rotation detection signal"). Referring now to FIG. 2, if the display 210 is rotated to be within a first angle range P1 of about 0 to 45 degrees with respect to a reference angle (e.g., 0 degree), then the rotation detecting unit 140 may output a first rotation detection signal. Also, if the display 210 is rotated to be within a second angle range P2 of about 45 to 90 degrees, then the detecting unit 140 may output a second rotation detection signal. In one embodiment, when the display 210 is rotated to be positioned at an angle of 45 degrees, the detecting unit 140 may output the second rotation detection signal.

The ultrasound system may further include a control unit 150. The control unit 150 may be configured to control transmission/reception of the ultrasound signals. Further, the control unit 150 may be operable to control formation of the ultrasound image and the touch screen menu. The control unit 150 may also be configured to determine a display mode of the ultrasound image and the touch screen menu on the display in response to the rotation detection signals.

Figure 3:
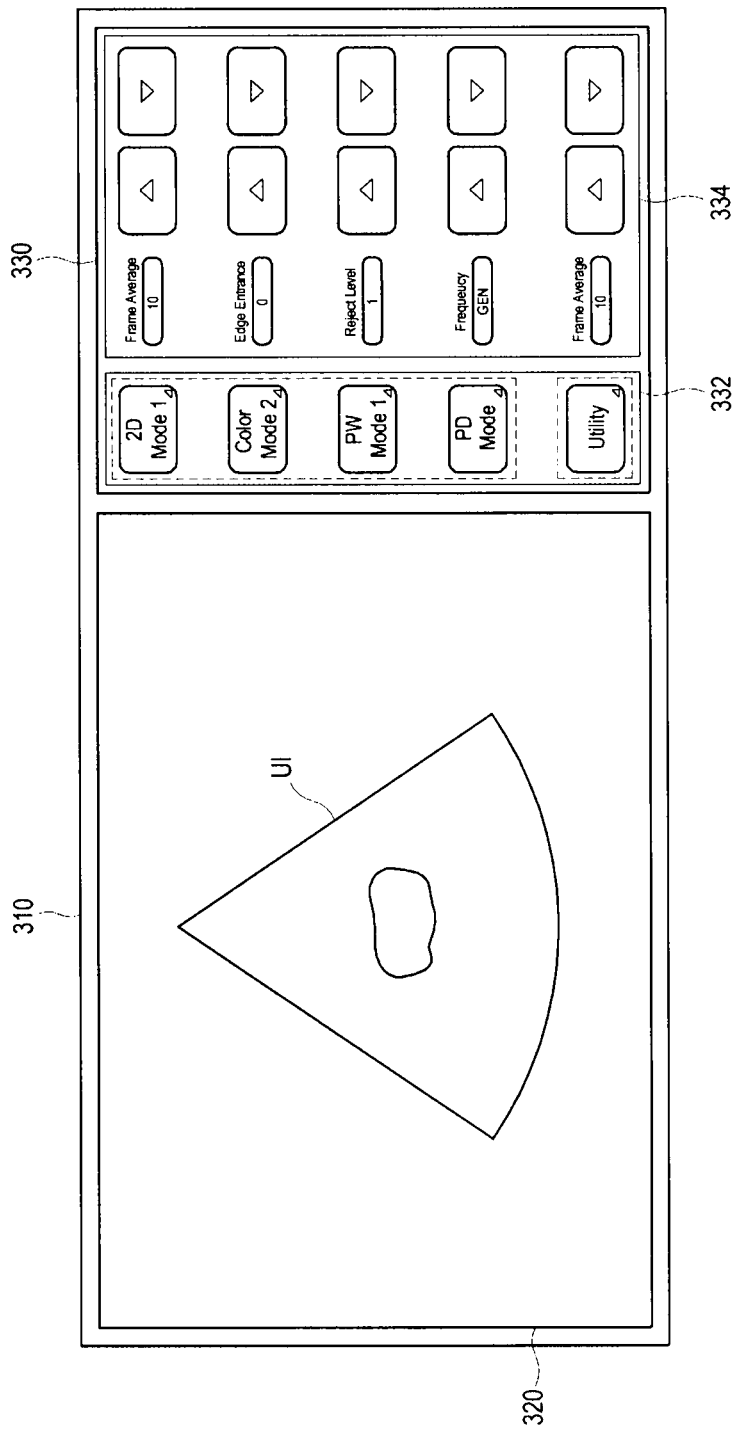
FIGS. 3-8 are schematic diagrams showing examples of displaying an ultrasound image and a touch screen menu.

In one embodiment, if the first rotation detection signal is outputted from the detecting unit 140, then the control unit 150 may be operable to control the display unit 130 such that a first display area 320 and a second display area 330 are displayed on left and right sides of the screen, respectively, as illustrated in FIG. 3. In such a case, the ultrasound image UI may be displayed on the first display area 320 and the touch screen menu may be displayed on the second display area 330. As described above, the touch screen menu may include the main menu 332 and the sub menu 334. In one embodiment, a ratio of the horizontal dimensions of the first display area 320 and the second display area 340 may be set to 3:1. However, the ratio is certainly not limited thereto. The size ratio may be adjusted according to the image mode.

In one embodiment, it has been described that the ultrasound image UI may be displayed on the first display area 320 and the touch screen menu may be displayed on the second display area 340. However, displaying the ultrasound image UI and the touch screen menu is certainly not limited thereto. In another embodiment, the touch screen menu may be displayed on the first display area 320 and the ultrasound image UI may be displayed on the second display area 330. In such a case, the ratio of the horizontal dimensions of the first display area 320 and the second display area 330 may be set to 1:3, although it is certainly not limited thereto.

Figure 4:
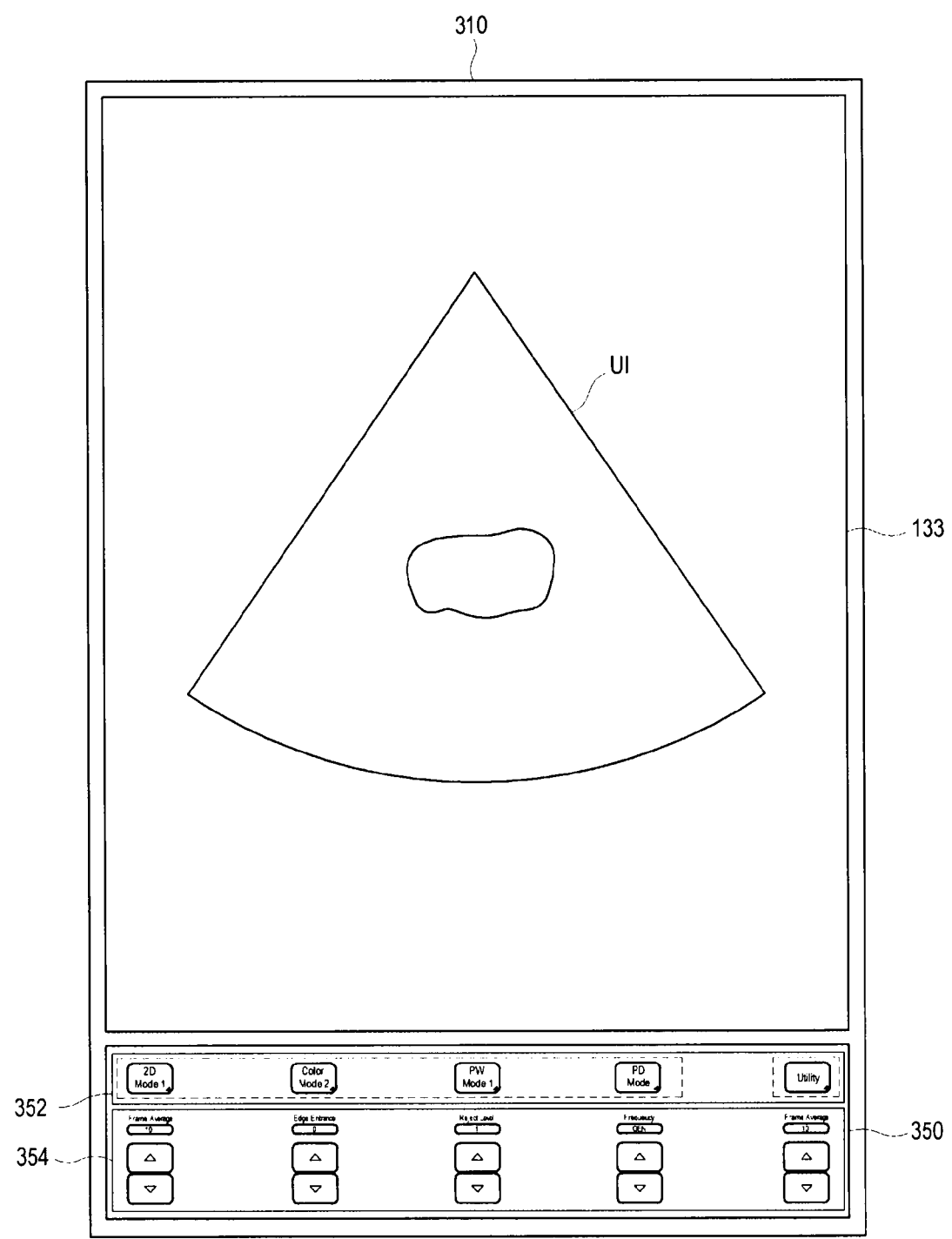

If the second rotation detection signal is outputted from the detecting unit 140, then the control unit 150 may be operable to control the display 310 such that a third display area 340 and a fourth display area 350 are displayed on upper and lower sides of the screen of the display 310, respectively, as illustrated in FIG. 4. In such a case, the ultrasound image UI may be displayed on the third display area 340 and the touch screen menu may be displayed on the fourth display area 350. The touch screen menu may include the main menu 352 and the sub menu 354. A ratio of the vertical dimensions of the third display area 340 and the fourth display area 350 may be set to 7:1. However, the ratio is certainly not limited thereto.

If the touch signal is inputted from the display unit 130, then the control unit 150 may be configured to control the ultrasound system 100 such that the function corresponding to the soft button located at the user touch is performed.

The ultrasound system 100 may further include an approach sensing unit 160. In one embodiment, the approach sensing unit 160 may be installed on a front side of the display unit 130. However, the location of the approach sensing unit 160 is not limited thereto. The approach sensing unit 160 may be operable to sense whether any object such as a user's hand, a stylus, etc. approaches the approach sensing unit 160 within a predetermined distance. If the object approaches within the predetermined distance, then the approach sensing unit 160 may output an approach sensing signal. Any device capable of sensing the approach of the object may be used as the approach sensing unit 160.

Figure 5:
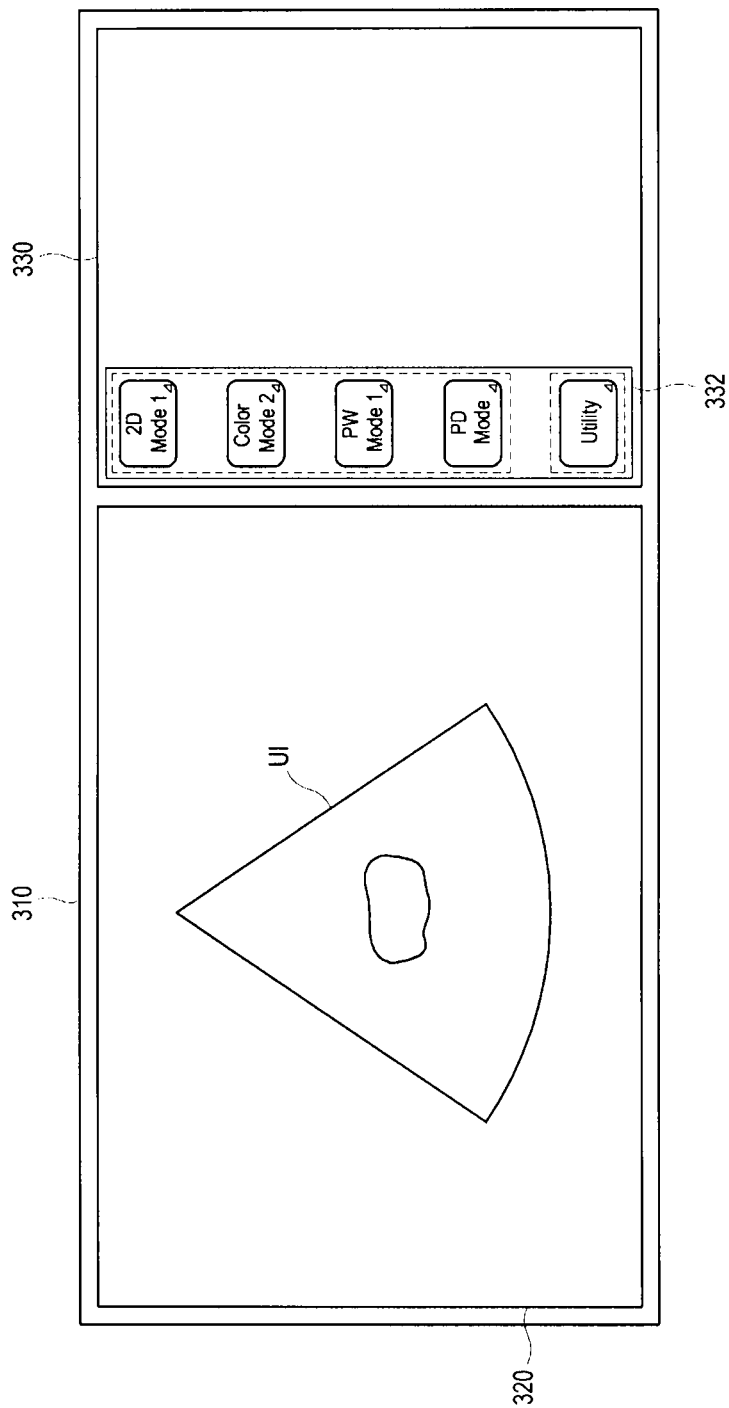

If the approach sensing signal is not outputted from the approach sensing unit 160, then the control unit 150 may be operable to control the display 310 such that the main menu is only displayed on the display unit 130, as illustrated in FIG. 5. In such a case, the display area 330 displaying the touch screen menu may be reduced depending on the size of the main menu 332. That is, the control unit 150 may control the display unit 130 such that the display area 320 for displaying the ultrasound image UI may be widened and the display area 330 for displaying the touch screen may be reduced. In another embodiment, If the approach sensing signal is not outputted, then the control unit 150 may be operable to control the display 310 such that the ultrasound image UI is only displayed.

Figure 6:
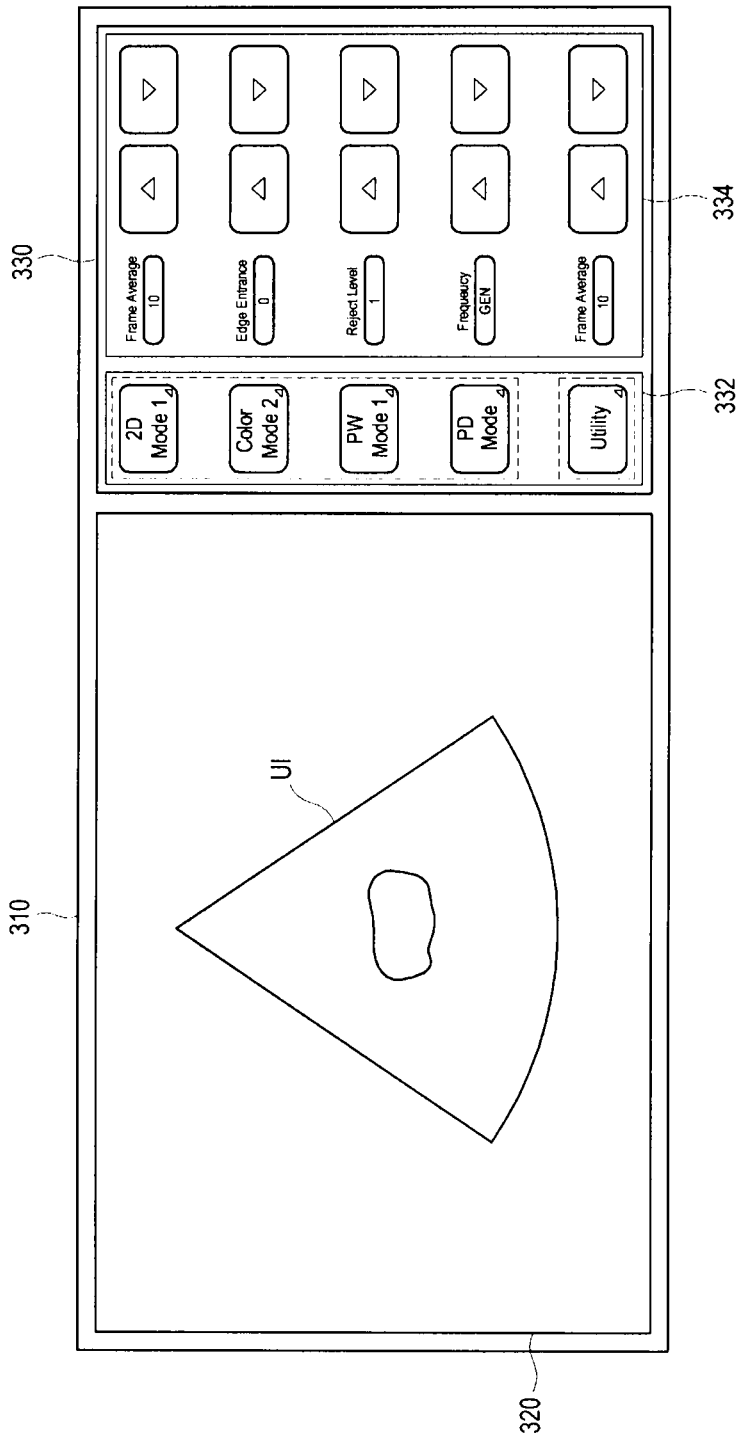

However, if the approach sensing signal is outputted from the approach sensing unit 160, then the control unit 150 may be operable to control the main menu 332 and the sub menu 334 to be displayed at the same time, as illustrated in FIG. 6. In such a case, the size of the display area 330 for displaying the touch screen menu may be adjusted according to the size of the main menu 332 and sub menu 334.

Figure 7:
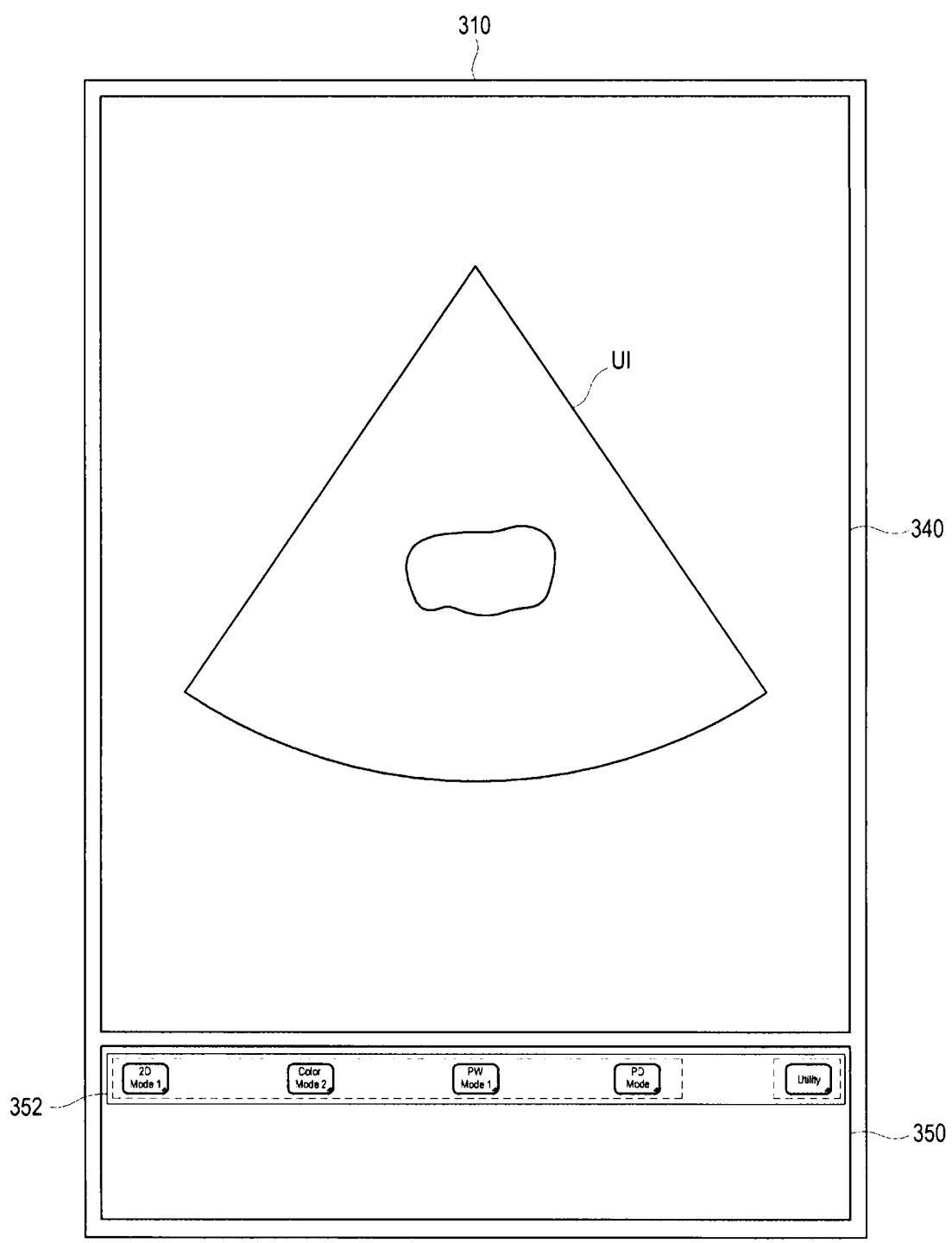
Figure 8:
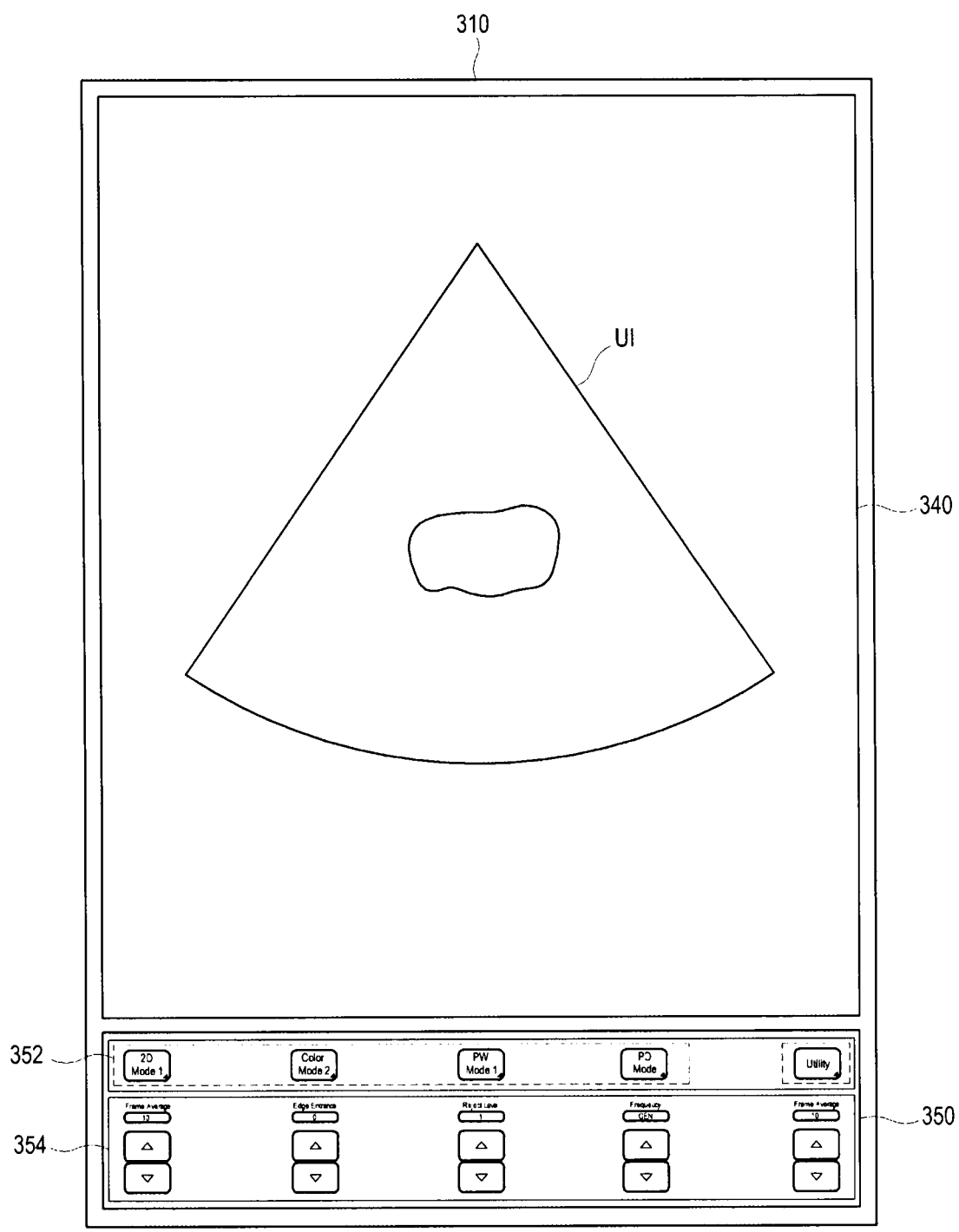

FIGS. 7 and 8 show examples of displaying the ultrasound image and the touch screen menu, while the display of the display unit 130 is rotated to be at an angle of 90 degrees. If the approach sensing signal is outputted from the approach sensing unit 160, then the control unit 150 may be operable to control the display 310 such that the main menu is only displayed on the display unit 130, as illustrated in FIG. 7. In such a case, the display area 350 displaying the touch screen menu may be reduced depending on the size of the main menu 352. That is, the control unit 150 may control the display unit 130 such that the display area 340 for displaying the ultrasound image may be widened and the display area 350 for displaying the touch screen may be reduced. Also, the control unit may be operable to control the display unit 130 such that the ultrasound image is only displayed while the approach sensing signal is not outputted in another embodiment.

However, if the second signal is outputted from the approach sensing unit 160, then the control unit 150 may be operable to control the main menu 352 and the sub menu 354 to be displayed at the same time, as illustrated in FIG. 8. In such a case, the size of the display area 350 for displaying the touch screen menu may be adjusted according to the size of the main menu 352 and sub menu 354.

In one embodiment, since the display unit and the user interface are embodied in a single device, costs may be reduced. Also, the touch screen menu is provided on the display together with the ultrasound image so that the user may easily select a desirable function of the ultrasound system without changing the user's sight. Further, since the touch screen menu is provided on a residual display area while the ultrasound image is displayed, the display area of the display unit 130 may be efficiently utilized.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound diagnostic unit configured to form an ultrasound image based on echoes reflected from a target object;
a touch screen menu forming unit configured to form a touch screen menu having graphics and text, the touch screen menu including hierarchically arranged soft buttons associated with functions of the ultrasound system;
a display unit including a display with a touch panel mounted, the display unit being configured to display the touch screen menu together with the ultrasound image on the display to prompt a user to touch a desired one of the soft buttons for triggering an execution of the associated function therewith, the display unit further including a support to rotatably support the display, the display unit further including an approach sensing unit configured to sense an approach of an object, and to output an approach sensing signal while the object is within a predetermined distance from the display;
a rotation detection sensor configured to detect rotation of the display to output a rotation detection signal; and
a controller configured to determine a display mode of the ultrasound image and the touch screen menu in response to the rotation detection signal, the controller configured to control the display to display the ultrasound image adjacent to a first side of the touch screen menu in response to a first rotation detection signal, and to display the ultrasound image adjacent to a second side of the touch screen menu in response to a second rotation detection signal, the first side and the second side being different, wherein
the display unit is further configured to divide a display area of the display into at least two display areas, and to display the touch screen menu on one of the two display areas based on the display mode in response to the approach sensing signal, and
the controller is further configured to control the display such that the ultrasound image is displayed while the approach sensing signal is not outputted, and the ultrasound image and the touch screen menu are displayed while the approach sensing signal is outputted from the approach sensor.

2. The ultrasound system of claim 1, wherein the rotation detection sensor is further configured to output the first rotation detection signal when the display is rotated within a range of 0 to 45 degrees, and wherein the rotation detection sensor is further configured to output the second rotation detection signal when the display is rotated within a range of 45 to 90 degrees.

3. The ultrasound system of claim 2, wherein the controller is further configured to control the display such that a first display area and a second display area are set on left and right sides on a screen of the display in response to the first detection signal, and wherein the ultrasound image is displayed on the first display area and the touch screen menu is displayed on the second display area.

4. The ultrasound system of claim 3, wherein the controller is further configured to control the display such that a third display area and a fourth display area are set on upper and lower sides on a screen of the display in response to the second detection signal, and wherein the ultrasound image is displayed on the third display area and the touch screen menu is displayed on the fourth display area.

5. An ultrasound system, comprising:
an ultrasound diagnostic unit configured to form at least one ultrasound image based on echoes reflected from a target object;
a touch screen menu forming unit configured to form a touch screen menu having graphics and text, the touch screen menu including hierarchically arranged soft buttons associated with functions of the ultrasound system;
a display unit including a display with a touch panel mounted, the display unit being configured to display at least one of the ultrasound image and the touch screen menu on the display; an approach sensor configured to sense an approach of an object, and to output an approach sensing signal while the object is within a predetermined distance from the display; a rotation detection sensor configured to detect rotation of the display to output a first detection signal when a longitudinal direction of the display is within a first angle range and to output a second detection signal when the longitudinal direction of the display is within a second angle range; and
a controller configured to control the display to divide a display area of the display into a left display area and a right display area to display the ultrasound image and the touch screen menu, respectively, in response to the first detection signal, and to divide the display area into an upper display area and a lower display area to display the ultrasound image and the touch screen menu, respectively, in response to the second detection signal, wherein the controller is further configured to control the display such that the ultrasound image is displayed while the approach sensing signal is not outputted, and the ultrasound image and the touch screen menu are displayed while the approach sensing signal is outputted from the approach sensor.

6. The ultrasound system of claim 5, wherein the first angle range is an angle range of 0 to 45 degrees, and the second angle range is an angle range of 45 degrees to 90 degrees.

7. The ultrasound system of claim 5, wherein the controller is further configured to control the display to enlarge the ultrasound image in response to the second detection signal.

8. An ultrasound system, comprising:
an ultrasound diagnostic unit configured to form at least one ultrasound image based on echoes reflected from a target object;
a display unit including a display with a touch panel mounted, the display unit being configured to display at least one of the ultrasound image and a touch screen menu on the display; an approach sensor configured to sense an approach of an object, and to output an approach sensing signal while the object is within a predetermined distance from the display; a rotation detection sensor configured to detect rotation of the display to output a first detection signal when a longitudinal direction of the display is within a first angle range and to output a second detection signal when the longitudinal direction of the display is within a second angle range; and
a controller configured to control the display to divide a display area of the display into at least two display areas in a horizontal direction to display at least two different ultrasound images, respectively, in response to the first detection signal, and to divide the display area of the display into at least two display areas in a vertical direction to display at least two different ultrasound images, respectively, in response to the second detection signal, wherein the controller is further configured to control the display such that the ultrasound image is displayed while the approach sensing signal is not outputted, and the ultrasound image and the touch screen menu are displayed while the approach sensing signal is outputted from the approach sensor.

9. The ultrasound system of claim 8, wherein the first angle range is an angle range of 0 to 45 degrees, and the second angle range is an angle range of 45 degrees to 90 degrees.

10. The ultrasound system of claim 8, wherein the controller is further configured to control the display to enlarge at least one of the ultrasound images in response to the second detection signal

* * * * *